(12) United States Patent
White

(10) Patent No.: US 6,932,821 B2
(45) Date of Patent: Aug. 23, 2005

(54) FEMORAL BROACH WITH UNDERCUT TEETH

(75) Inventor: Patrick Michel White, Downington, PA (US)

(73) Assignee: Precimed S.A., Orvin (CH)

( * ) Notice: Subject to any disclaimer, the term of this patent is extended or adjusted under 35 U.S.C. 154(b) by 0 days.

(21) Appl. No.: 10/670,633

(22) Filed: Sep. 25, 2003

(65) Prior Publication Data

US 2004/0116933 A1 Jun. 17, 2004

Related U.S. Application Data

(60) Provisional application No. 60/414,833, filed on Sep. 28, 2002.

(51) Int. Cl.$^7$ ............................................. A61B 17/32
(52) U.S. Cl. ...................................................... 606/85
(58) Field of Search ............................. 606/79, 80, 81, 606/82, 84, 85, 99, 167; 408/227, 228, 229, 230, 231; 132/76.4, 76.5

(56) References Cited

U.S. PATENT DOCUMENTS

| | | | |
|---|---|---|---|
| 4,765,328 A | * | 8/1988 | Keller et al. ................... 606/85 |
| 4,872,452 A | | 10/1989 | Alexson |
| 5,006,121 A | | 4/1991 | Hafeli |
| 5,041,118 A | | 8/1991 | Wasilewski |
| 5,169,401 A | * | 12/1992 | Lester et al. ................... 606/79 |
| 5,261,915 A | * | 11/1993 | Durlacher et al. ............. 606/85 |
| 5,342,365 A | | 8/1994 | Waldman |
| 5,665,091 A | | 9/1997 | Noble et al. |
| 5,681,315 A | * | 10/1997 | Szabo ........................... 606/85 |
| 5,897,558 A | | 4/1999 | Frieze et al. |
| 6,319,256 B1 | | 11/2001 | Spotorno et al. |
| 2002/0019638 A1 | * | 2/2002 | Grimard et al. ............... 606/85 |

FOREIGN PATENT DOCUMENTS

| | | |
|---|---|---|
| DE | 27 32 325 | 1/1979 |
| DE | 298 16 064 | 11/1998 |
| EP | 0 378 002 | 7/1990 |
| EP | 0 733 343 | 9/1996 |
| EP | 1 033 108 | 9/2000 |
| FR | 2 722 391 | 1/1996 |
| WO | WO 01 08571 | 2/2001 |

OTHER PUBLICATIONS

Standard Search Report IN SN RS 109339.

* cited by examiner

Primary Examiner—Eduardo C. Robert
Assistant Examiner—David Comstock
(74) Attorney, Agent, or Firm—Bugnion S.A.; John Moetteli

(57) ABSTRACT

An elongated cutting tool (10, 110) intended to plunge cut a blind form in a bone using a plurality of teeth (30, 130) arranged on the tool. At least one of the teeth is an undercut tooth (30, 130) having a cutting edge (470, 570). The undercut tooth (30, 130) has a profile defined substantially along a primary relief angle (480, 580) measured from a vertical reference plane (477, 577) passing though the cutting edge (470, 570) and by a positive rake angle (485, 585) measured from a horizontal reference plane (472, 572) passing through the cutting edge (470, 570). The undercut tooth (30, 130) has a parabolic, non-circular relief (490, 590) along which bone chips are guided substantially away from the bone being cut, thereby avoiding capturing debris in the teeth and, consequently, avoiding overstressing the bone during cutting.

9 Claims, 3 Drawing Sheets

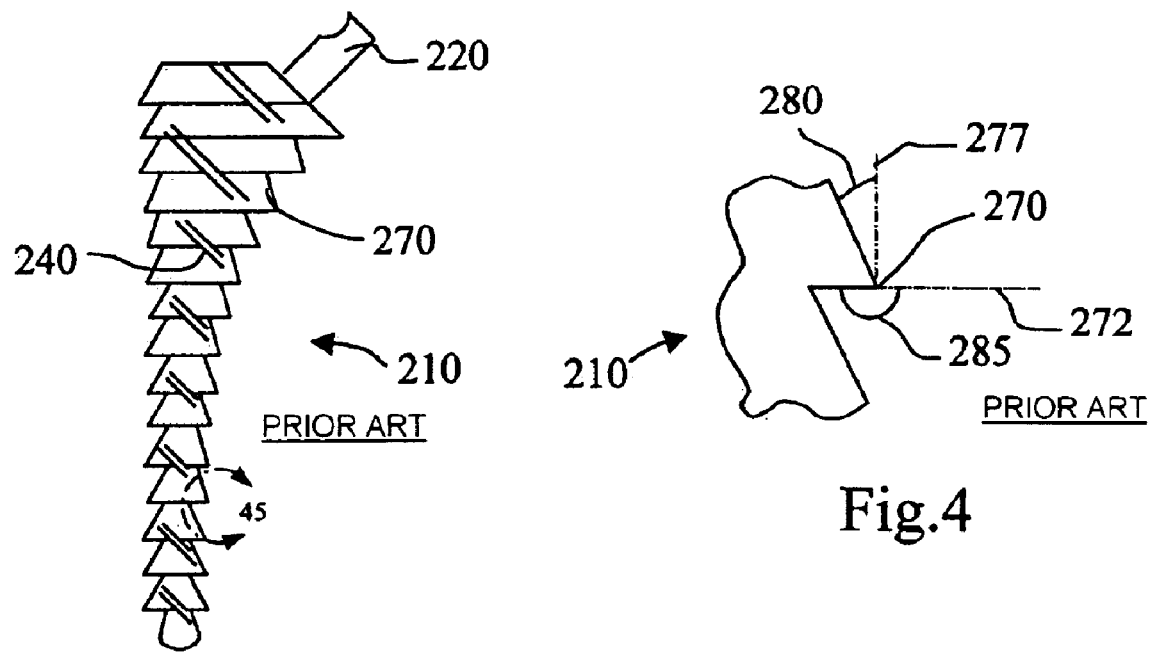
Fig.3 PRIOR ART
Fig.4 PRIOR ART
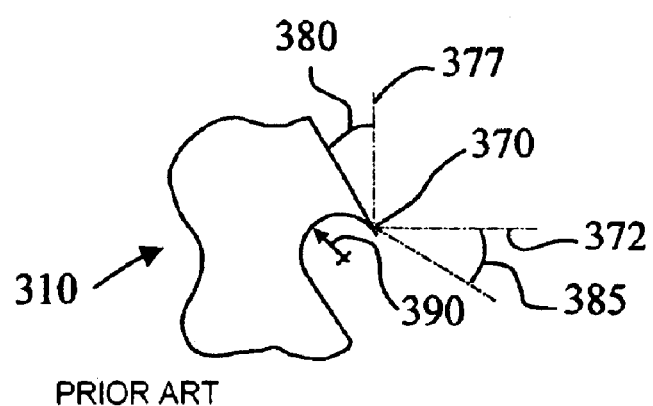
Fig.5 PRIOR ART

FEMORAL BROACH WITH UNDERCUT TEETH

This application claims the benefit of provisional application No. 60/414,833, filed Sep. 28, 2002.

BACKGROUND OF THE INVENTION

This invention relates to femoral rasps and broaches useful for the removal of tissue and bone from inside the femoral canal during reconstructive joint surgery.

Orthopedic surgeons have become quite familiar with using cutting instruments to clear out the inside of the femoral canal during joint reconstructive surgery. In most cases, surgeons use a rasp or broach to prepare the canal for a femoral implant replacement. A femoral broach is designed to have a complex surface which corresponds to the implant shape and has teeth generally perpendicular to the axis of the femur. One of the difficulties using broaches occurs in the medial calcar region of the femur where there is a sharp change in the internal geometry of the femur. To cut this area of the bone, the geometry of the broach flares out exposing the underside of the cutting teeth which are normally flat. As the broach is impacted, the flat surfaces tend to compress the bone, rather than cut it. This compression induces internal stresses in the bone which can build up until the proximal portion of the femur fractures, creating complications for the surgeon. Several attempts to reduce the risk of calcar fracture have been implemented. In some cases the surgeons place a circlage wire around the femur to help the femur resist excessive hoop stresses caused by the broach. The theory behind this surgical step is that the wire will help strengthen the bone and alleviate the stress; however, this wire is an additional expense for the surgery and takes extra time to implement during the procedure.

The cutting teeth in one broach system have a positive rake angle, to increase the tooth's cutting capability. Generally, this operates well. However, during fabrication, in order to create the undercut teeth, a milling cutter is used having a spherical tip. These milling tools have limitations due to their size, and as a result, broaches manufactured with this process have fewer and larger teeth with which to form the cutting profile, resulting in a less accurately defined final envelope for the implant. The larger undercut teeth, while having the advantage of being able to cut well, have not had much commercial success because of their lack of sufficient accuracy. Also, these broaches have a spherical or round relief on the teeth due to the necessary geometry of the cutting tools used to manufacture them. The round relief is not ideal for quickly directing material away from the cutting site (which is desirable in order to avoid bone chips from becoming trapped in the teeth), once again increasing the stress in the bone and consequently adding to the risk of femur fracture. To alleviate the trapping of the bone chips, chip breakers are often added in the teeth which allow the chips to be pushed upward upon advancement of the broach. However, adding chip breakers alone is not a sufficient solution because most broach systems that have chip breakers are still experiencing femur breakage.

Others have approached the problem from another direction by placing the teeth on the cutting surface in a manner similar to that of a wood rasp. These teeth generally have a diamond shape. In order to cut across its entire surface, these broaches have a multiplicity of discrete teeth, as does a wood rasp. The diamond shape pattern helps create more clearance for chips to pass in an attempt to reduce the pressure on the bone, hence decreasing the femoral fracture rate. However, because the teeth are positioned in a discrete fashion, they tend to tear the bone and tissue rather than cutting it. As a result, debris lodges in between the teeth, thereby rendering the rasps less effective in shaping the femoral canal. Some companies have tried to overcome these problems by increasing their tooth depth and others have arranged the teeth in a progressive helical pattern, but this has not addressed the issue of the teeth tearing the bone.

Therefore, there is a need for a surgical broaching tool which accurately shapes the inside of the femoral canal while avoiding placing extensive pressure on the bone. There is a further need for a femoral broach that does not have a flat underside to the tooth. Still further, there is a need for a tooth with a noncircular rake enabling the teeth to be undercut in order to cut efficiently and help remove the bone chips from the cutting site. There is a further need still to have a femoral broach with a tooth that is undercut with a non circular rake wherein the tooth size is reduced to increase the accuracy of the broached cavity. Still further, there is a need to have a broach with teeth that are designed to alleviate the trapping of the bone chips during use. There is also a need to have a femoral rasp whose teeth cut the bone efficiently, rather than collecting bone chips under the teeth.

BRIEF DESCRIPTION OF DRAWINGS

The attached drawings represent, by way of example, different embodiments of the subject of the invention.

FIG. 3 is a side view of a femoral broach as depicted in FIG. 1 with broach teeth of the prior art.

FIG. 4 is a section view more closely showing the prior art tooth detail of FIG. 3.

FIG. 5 is a section view of FIG. 3 showing an alternative tooth detail of the prior art with a positive rake angle formed by a spherical milling tool.

DETAILED DESCRIPTION OF DRAWINGS

Figure 1:
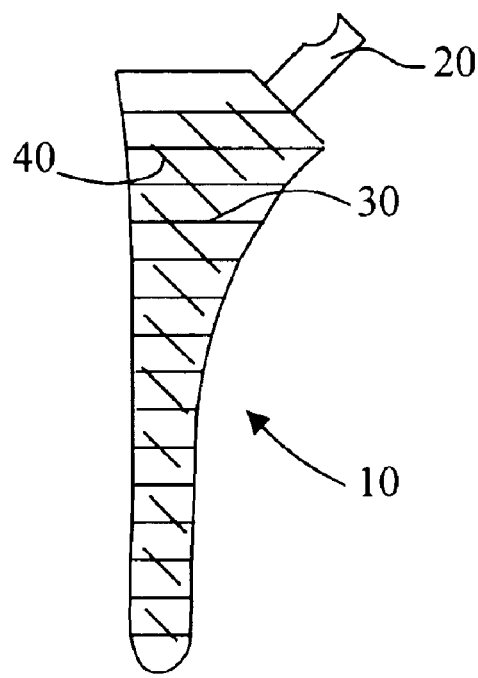
FIG. 1 is a side view of a femoral broach with horizontal teeth and chip breakers.

Referring now to FIG. 1, a femoral broach 10 is shown having a handle interface 20 for attaching to a modular handle. The modular handle (not shown) is used for impaction of the broach 10 into the canal and for retracting the broach during removal from the femur. After the broach 10 is fully seated in the canal, the handle is released from the interface 20. This frees the broach 10 up to be used as a trial and the interface 20 is commonly used as a guide for a calcar reamer to trim the bone in preparation for mounting of the collar of an implant. The interface is also useful for supporting the provisional necks which correspond to the implant neck length while trialing the construct to ensure proper sizing and placement of the implant in relationship to the cleared femoral canal. In some cases companies have provided the handle integral with the broach 10 in which case the handle interface 20 would not be present. The teeth 30 are arranged generally in a horizontal orientation and chip breakers 40 (for example, those shown in U.S. Pat. No. 5,665,091 to Noble, the content of which is incorporated by reference hereto) relieve the construct in an attempt to allow material to pass through the teeth and to give some relief so that all of the cutting edges aren't contacting the bone at the same time. The teeth 30 and chip breakers 40 shown in FIG. 1 are presented in a typical pattern of a broach style instrument. Broaches of the prior art and of the present invention have teeth arranged in similar patterns on the surface of the broach 10 as shown herein.

Figure 2:
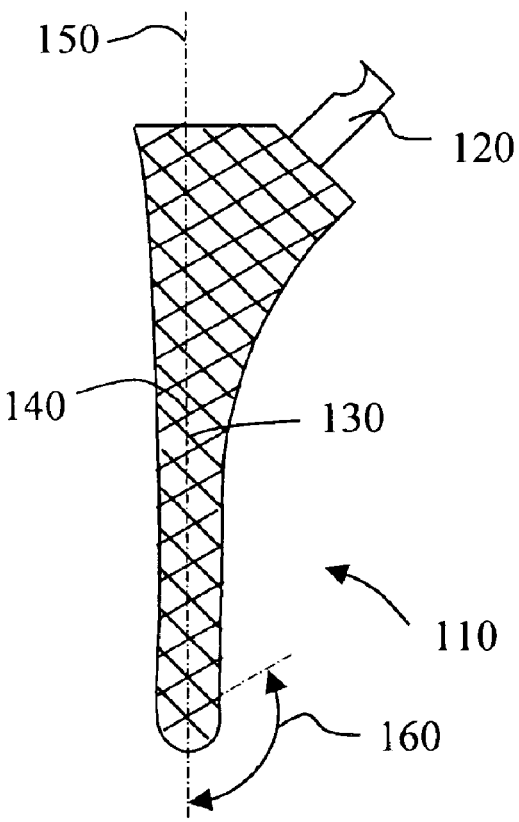
FIG. 2 is a side view of a femoral rasp with diamond teeth.

Referring now to FIG. 2 which shows a second embodiment of the present invention, a femoral rasp 110 has a handle interface 120 for attaching to a modular handle. The modular handle (not shown) is used for impaction of the rasp 110 into the canal and for retracting the rasp during removal from the femur. After the rasp 110 is fully seated in the canal, the handle is released from the interface 120. This frees the rasp 110 up to be used as a trial of the construct and the interface 120 is commonly used as a guide for a calcar reamer to trim the bone thereby preparing it for the collar of an implant. The interface is also useful for supporting the provisional necks which correspond to the implant neck length while trialing the construct to ensure proper sizing and placement of the implant in relationship to the cleared femoral canal. In some cases, companies have provided the handle integral with the rasp 110 in which case the handle interface 120 would not be present. The teeth 130 and 140 are arranged generally in a diamond shape pattern which is oriented at an angle 160 in relationship to the drive axis 150. On some of the more modern designs, this angle can represent a helix and the teeth may be presented on the surface in a helical pattern. Others have arranged the teeth so they progressively increase in size along the helix. The types of teeth 130 and 140 shown in FIG. 2 are presented in a typical pattern of a rasp style instrument. Rasps of the prior art and of the present invention have teeth arranged in similar patterns on the surface of the rasp 110 as shown herein.

Referring now to FIG. 3, a femoral broach 210 and a handle interface 220 for attachment to a modular handle of the prior art is shown. The teeth 270 are arranged in a similar pattern as shown in FIG. 1 and chip breakers 240 are arranged along the cutting surface.

Referring now to FIGS. 4–5, section views of FIG. 3 show typical teeth of the prior art. The broach 210 has a cutting edge 270 with horizontal reference 272 and vertical reference 277 taken in relation to the cutting edge 270. The primary relief angle 280 is located off of the vertical reference 277 and the rake angle 285 is taken off the horizontal reference 272 which is shown at zero degrees. Because the rake angle 285 is flat, this tooth style has difficulty because the bottom of the tooth compresses the bone during use. As an alternative, the broach 310 has a cutting edge 370 with horizontal reference 372 and vertical reference 377 taken in relation to the cutting edge 370. The primary relief angle 380 is located off of the vertical reference 377 and the rake angle 385 is taken off the horizontal reference 372 which is shown with a positive angle. When this broach 310 is impacted into the bone, the edge 370 cuts more efficiently than the edge 270 as shown in FIG. 4. However, when the bone is cut, it tends to trap in the circular or spherical relief 390 which still acts as a shelf for the bone. The relief 390 is formed with a milling tool and the typical size is somewhere around 0.125 inches in diameter. It is difficult to use a milling tool to create a smaller, shallower tooth having an undercut with a positive rake angle 385.

Figure 6:
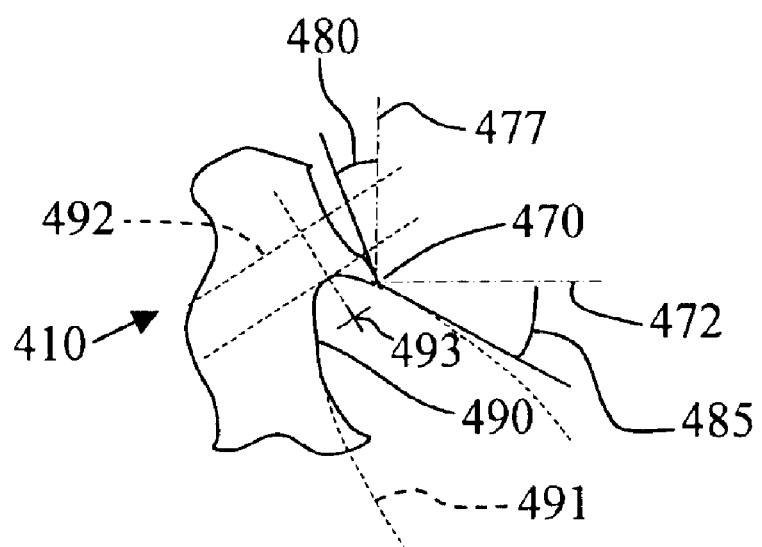
FIG. 6 is a section view showing the tooth detail of the present invention with a positive rake angle formed by a generally parabolic relief.

Referring now to FIG. 6, a preferred embodiment of the present invention is shown in which the broach 410 has a cutting edge 470 with horizontal reference 472 and vertical reference 477 taken in relation to the cutting edge 470. The primary relief angle 480 is located off of the vertical reference 477 and the rake angle 485 is taken off the horizontal reference 472 which is shown with a positive angle. The relief 490 has an apex area (the section where the dashed parabola of FIGS. 6 and 7 and the tooth profile overlap) having a a parabolic, non circular shape 491. This type of relief 490, having in this example, a directrix 492, and focus 493, is made possible by new manufacturing processes such as EDM, chemical machining, highly controlled laser cutting (although broaching is also possible). A tooth style as shown in FIG. 6 can be used in conjunction with typical tooth patterns of conventional broaches and rasps as described in FIGS. 1–2. The features of this style tooth give the user the benefit of the undercut tooth with positive rake 485 along with the combined efficiency of the unique relief 490 which is designed to clear the bone chips more effectively to avoid capturing the debris in the teeth. When placed on a broach style tool as in FIG. 1, the parabolic non-circular relief 490 acts to move the cut bone away from the teeth more effectively, thereby creating a more efficient cut and in turn reducing the pressure on the bone during use. When placed on a rasp style tool as in FIG. 2, the positive rake angle 485 aids in cutting the bone rather than tearing it.

Figure 7:
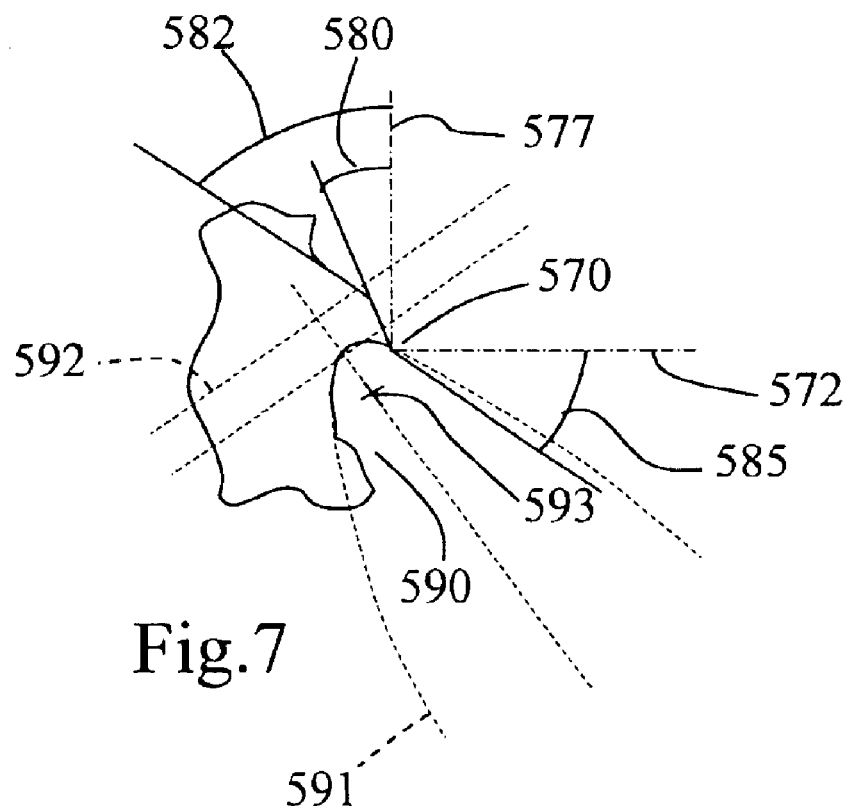
FIG. 7 is a section view showing an alternative tooth detail of the present invention having a primary and secondary relief angle, the tooth also having a positive rake angle formed by a generally parabolic relief.

Referring now to FIG. 7, a broach 510 is shown having a cutting edge 570 with horizontal reference 572 and vertical reference 577 taken in relation to the cutting edge 570. The primary relief angle 580 is located off of the vertical reference 577 along with a secondary relief 582. The rake angle 585 is taken off the horizontal reference 572 which is shown having a positive angle. The relief 590 takes the form of a unique parabolic or non circular shape 591. This type of relief 590, having in this example, a directrix 592, and focus 593, is made possible by new manufacturing processes such as EDM, chemical machining or highly controlled laser by new manufacturing processes such as EDM, chemical machining or highly controlled laser cutting. A tooth style as shown in FIG. 7 can be used in conjunction with typical tooth patterns of conventional broaches and rasps as described in FIGS. 1–2. The features of this style tooth give the user the benefit of the undercut tooth with positive rake 585 along with the combined efficiency of the unique relief 590 and the secondary relief 582 which are designed to clear the bone chips more effectively to avoid capturing the debris in the teeth. When placed on a broach style tool as in FIG. 1, the parabolic non-circular relief 590 and the secondary relief 582 act to move the cut bone away from the teeth, thereby effectively creating a more efficient cut and in turn reducing the pressure on the bone during use. When placed on a rasp style tool as in FIG. 2, the positive rake angle 585 aids in cutting the bone rather than tearing it.

It is recognized that femoral cutting tools having teeth with non-circular shaped cutting relief and a positive rake angle provide benefits to the surgeon by reducing the risk of femoral fractures during use. It is also recognized that the addition of a secondary relief adds to these benefits. These types of teeth formed through EDM, chemical, or laser machining (or broaching) can be applied to various other cutting tools including hollow broaches where the inside of the broach is fashioned to catch the cut debris along with acetabular reamers which are designed to accomplish the same while cutting bone. It will be apparent from the foregoing that while particular forms of the invention have been illustrated and described, various modifications can be made without departing from the spirit and scope of the invention. Accordingly it is not intended that the invention be limited, except as stated in the appended claims.

Although illustrative embodiments of the invention have been shown and described, a wide range of modification, change and substitution is contemplated in the foregoing disclosure and in some instances, some features of the present invention may be employed without a corresponding use of the other features. Accordingly, it is appropriate that the appended claims be construed broadly and in a manner consistent with the scope of the invention.

What is claimed is:

1. An elongated cutting tool intended to plunge cut a blind form in a bone using a plurality of teeth (30, 130) arranged on the tool, at least one of the teeth being an undercut tooth (30, 130) having a cutting edge (470, 570), the undercut tooth (30, 130) having a profile defined substantially along a primary relief angle (480, 580) measured from a vertical reference plane (477, 577) passing though the cutting edge (470, 570) and by a positive rake angle (485, 585) measured from a horizontal reference plane (472, 572) passing through the cutting edge (470, 570), wherein the undercut tooth has a non-circular relief (490, 590) having an apex area which is parabolic in shape, along which bone chips are guided substantially away from the bone being cut, thereby avoiding capturing debris in the teeth and, consequently, avoiding overstressing the bone during cutting.

2. The tool of claim 1, wherein the tool is a broach.

3. The tool of claim 2, wherein the tool includes at least one chip breaker (40, 140).

4. The tool of claim 1, wherein the tool is a rasp.

5. The tool of claim 4, wherein the teeth (130, 140) are arranged generally in a diamond shape pattern oriented at an angle (160) in relationship to a drive axis (150).

6. The tool of claim 5, wherein the angle is formed in a helix in which the teeth are disposed about the tool in a helical pattern.

7. The tool of claim 6, wherein the teeth are arranged so as to progressively increase in size along the helix.

8. The tool of claim 1, wherein the tool includes at least one chip breaker (40, 140).

9. The tool of claim 1, wherein a handle interface (220) is provided for attachment to a modular handle interface.

* * * * *